United States Patent [19]

Juneja

[11] 4,198,392

[45] Apr. 15, 1980

[54] ORAL COMPOSITIONS CONTAINING BIS-BIGUANIDES WITH REDUCED STAINING TENDENCIES

[75] Inventor: Prem S. Juneja, Cincinnati, Ohio

[73] Assignee: The Procter & Gamble Company, Cincinnati, Ohio

[21] Appl. No.: 922,136

[22] Filed: Jul. 5, 1978

Related U.S. Application Data

[63] Continuation of Ser. No. 830,226, Sep. 2, 1977, abandoned, which is a continuation-in-part of Ser. No. 670,518, Mar. 24, 1976, abandoned, which is a continuation-in-part of Ser. No. 589,232, Jun. 23, 1975, abandoned.

[51] Int. Cl.$^2$ ............... C07C 129/08; A61K 31/155; A61K 7/18; A61K 9/68
[52] U.S. Cl. ........................... 424/48; 424/52; 424/54; 424/316; 424/326; 260/501.14; 260/565
[58] Field of Search ............... 260/565, 501.14; 424/48, 52, 54, 326, 316

[56] References Cited

U.S. PATENT DOCUMENTS

| | | | |
|---|---|---|---|
| 2,783,210 | 2/1957 | Kennerly | 252/401 |
| 3,925,543 | 12/1975 | Donohue | 424/52 |
| 3,934,002 | 1/1976 | Haefele | 424/54 |
| 3,937,807 | 2/1976 | Haefele | 424/52 |
| 4,001,393 | 1/1977 | L'Orange | 424/52 |
| 4,025,616 | 3/1977 | Haefele | 424/52 |
| 4,067,962 | 1/1978 | Juneja | 424/52 |

FOREIGN PATENT DOCUMENTS

| | | | |
|---|---|---|---|
| 233215 | 6/1959 | Australia | 424/54 |
| 168176 | 12/1976 | Belgium | 260/565 |
| 854514 | 9/1977 | Belgium | 260/565 |
| 533341 | 11/1956 | Canada | 260/565 |

OTHER PUBLICATIONS

Warner et al., J. Pharm. Science, vol. 62, (No. 7), pp. 1189-1191, (1973).
Turesky et al., J. Periodontal, vol. 77, No. 11, pp. 709-711, (1973).
Warner et al., Journal of Medicinal Chemistry, vol. 16, No. 6, pp. 732-733, (1973).
Emilson et al., Cories Res., vol. 10, pp. 352-362, (1976).

*Primary Examiner*—Joseph E. Evans
*Assistant Examiner*—L. Hendriksen
*Attorney, Agent, or Firm*—Ronald L. Hemingway; Douglas C. Mohl; Richard C. Witte

[57] ABSTRACT

Oral compositions such as toothpastes, mouthwashes, and the like containing particular substantive bis-biguanide compounds which inhibit the formation of plaque and caries.

15 Claims, No Drawings

ORAL COMPOSITIONS CONTAINING BIS-BIGUANIDES WITH REDUCED STAINING TENDENCIES

CROSS REFERENCE TO RELATED APPLICATION

This is a continuation of application Ser. No. 830,226, filed Sept. 2, 1977, which in turn is a continuation-in-part of the copending application of Prem S. Juneja having Ser. No. 670,518, filed Mar. 24, 1976, now abandoned which is in turn a continuation-in-part of the abandoned application of Prem S. Juneja having Ser. No. 589,232, filed June 23, 1975.

BACKGROUND OF THE INVENTION

The field of this invention is "oral compositions" which term is used herein to designate products which in the ordinary course of usage are retained in the oral cavity for a time and in a manner sufficient to contact essentially all of the dental surfaces, but are not intentionally ingested. Such products include, for example, dentifrices, mouthwashes, prophylaxis pastes and topical solutions.

The bis-biguanide antibacterial agents such as chlorhexidine, 1,6 bis($N^5$-p-chlorophenyl-$N^1$-biguanido)hexane, are known to be effective antiplaque agents, but it has been recognized that they have a tendency to produce severe staining of the teeth. Haefele; U.S. Pat. No. 3,934,002; issued Jan. 20, 1976 and Haefele; U.S. Pat. No. 4,025,616; issued May 24, 1977, disclose the use of the insoluble salts of the bis-biguanides in oral compositions as a means of reducing the stain problem. Haefele; U.S. Pat. No. 3,937,807; issued Feb. 10, 1976; U.S. patent application Ser. No. 681,867, filed Apr. 29, 1976 and U.S. patent application Ser. No. 817,076, filed July 18, 1977, disclose the use of metal ion chelator compounds, such as amino acids, aminopolycarboxylates and hydroxypyrones, with the bis-biguanides to reduce stain.

DESCRIPTION OF THE INVENTION

It has now been discovered that certain specific bis-biguanide compounds disclosed herein are effective antiplaque agents and do not have the tendency to cause the severe staining of the teeth, which was previously thought to be characteristic of all bis-biguanides which were effective antiplaque agents.

The bis-biguanide compounds of this invention have the generic formula

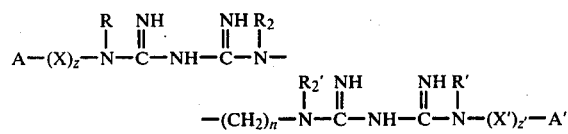

wherein A and A' each represent a phenyl radical which is substituted by one or more halogen (e.g., fluorine, chlorine or bromine), nitro, hydroxyl, $C_1$ to $C_6$ alkyl or $C_1$ to $C_6$ alkoxy groups; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms, wherein $R_2$ and $R_2'$ each represent hydrogen or alkyl of 1 to 2 carbon atoms and wherein n is an integer from 2 to 4. Preferred compounds are those wherein A and A' are chlorophenyl groups, z and z' are each 0 and R, R', $R_2$ and $R_2'$ are hydrogen and n is 2. Even more preferred compounds are those wherein A and A' are fluorophenyl groups, z and z' are each 0, R, R', $R_2$ and $R_2'$ are hydrogen and n is 2.

The pharmaceutically acceptable salts of the above compounds are especially desirable. The water soluble salts, especially the dihydrochloride, digluconate and diacetate salts, are the most desirable since they make possible the formation of clear solution compositions. In contrast with chlorhexidine, whose dihydrochloride salt is insoluble in water, the hydrochlorides of the compounds of the present invention are water-soluble. Typically, the hydrochloride salt is inherently formed in the preparation of chlorhexidine and of the compounds of the present invention. For purposes of this application, water-soluble salts are considered to be those having a solubility of greater than about 0.04% by weight in water at 25° C.

As indicated in the U.S. patents and patent applications cited supra, it was previously thought that all of the bis-biguanides which had substantial antiplaque activity also had a high tendency to stain the teeth, and that to be used in oral hygiene they had to be insolubilized in the form of insoluble salts or used in conjunction with a metal ion chelating agent in order to give an acceptably low level of tooth staining. However, in accordance with the present invention, it has been discovered that the specific bis-biguanides described above are effective antiplaque agents and product much less staining of the teeth than, for example, chlorhexidine, even without conversion to the insoluble salts or formulation with metal ion chelating agents. Accordingly, the compounds of the present invention can be used in oral hygiene in the substantial absence of metal ion chelators or materials which will form insoluble salts with said compounds.

Examples of bis-biguanides falling within the scope of the present invention are the following:

1,2-bis($N^5$-p-chlorophenyl-$N^1$-biguanido)ethane,
1,2-bis($N^5$-p-nitrophenyl-$N^1$-biguanido)ethane,
1,2-bis($N^5$-p-hydroxyphenyl-$N^1$-biguanido)ethane,
1,2-bis($N^5$-p-chlorobenzyl-$N^1$-biguanido)ethane
1,2-bis($N^5$-p-bromophenyl-$N^5$-hexyl-$N^1$-biguanido)ethane,
1,2-bis($N^5$-p-chlorophenyl-$N^5$-2-ethylphenyl-$N^1$-biguanido)ethane,
1,2-bis($N^5$-p-chlorophenyl-$N^1$-ethyl-$N^1$-biguanido)ethane,
1,2-bis($N^5$-p-methoxyphenyl-$N^1$-biguanido)ethane,
1,2-bis($N^5$-p-methylphenyl-$N^1$-biguanido)ethane,
1,2-bis($N^5$-3,5-dimethylphenyl-$N^1$-biguanido)ethane,
1,2-bis($N^5$-2,6-dichlorophenyl-$N^1$-biguanido)ethane,
1,2-bis($N^5$-2,6-dimethylphenyl-$N^1$-biguanido)ethane,
1,4-bis($N^5$-p-chlorophenyl-$N^1$-biguanido)butane,
1,3-bis($N^5$-p-chlorophenyl-$N^1$-biguanido)propane,
1,2-bis($N^5$-p-fluorophenyl-$N^1$-biguanido)ethane,
1,2-bis($N^5$-m-fluorophenyl-$N^1$-biguanido)ethane,
1,3-bis($N^5$-p-fluorophenyl-$N^1$-biguanido)propane, and
1,4-bis($N^5$-p-fluorophenyl-$N^1$-biguanido)butane and their water-soluble salts, for example, the digluconate, dihydrochloride and diacetate salts. In the foregoing exemplary compounds, the substituent groups on the phenyl ring can be in positions other than those shown, i.e., ortho, meta and para substitutions are suitable. A single substituent in the para position is preferable. The most preferred compounds are 1,2-bis(N$^5$-p-chlorophenyl-N$^1$-biguanido)ethane and its dihydrochloride, diacetate and digluconate salts and the novel compounds 1,2-bis(N$^5$-p-fluorophenyl-N$^1$-biguanido)ethane and its dihydrochloride, diacetate and digluconate salts.

The compounds of the invention can be made by reacting ethylene diamine dihydrochloride (or an appropriately N,N′ substituted ethylene diamine hydrochloride) with sodium dicyanamide to give a bis(N$^3$-cyano-N$^1$-guanidino)ethane, which is then reacted with the hydrochloride of the desired phenylamine hydrochloride to give the desired bis-biguanide compound in the form of its hydrochloride salt. The preparation procedure is well known in the art; see, for example, Warner et al, J. Pharm. Sci. 62 No. 7, 1189-91 (1973) and Rose et al, J. Chem. Soc. 4422 (1936).

The compositions of the present invention comprise from about 0.01% to about 2.5% (preferably from about 0.05% to about 1.2%, and most preferably from about 0.1% to about 0.8%) by weight of the bis-biguanide antiplaque agent and the balance, a carrier suitable for use in the oral cavity. All percentages herein are by weight, unless specified otherwise. Depending upon the composition, lesser or greater amounts may be used. In general, all that is required is to have an effective amount of the bis-biguanide salt in the mouth sufficient to give antiplaque and/or anticaries effectiveness. Generally, an amount of 0.001 grams or more per usage of the bis-biguanide can be considered as an effective amount for plaque control.

The pH of the compositions of this invention is preferably maintained within the range of from about 4.5 to about 9.5. Below about 4.5, damage to dental enamel can occur. Above about 9.5, the alkalinity becomes cosmetically undesirable and may irritate soft tissue in the mouth.

The compositions of the present invention comprise the aforedescribed bis-biguanide antiplaque agents and a carrier suitable for use in the oral cavity. The carrier can be water or an organic solvent such as alcohol. Preferably, however, the carrier portion of the oral composition is a conventional toothpaste, mouthwash, chewing gum or the like.

Dentifrices contain an abrasive polishing material and typically also contain sudsing agents, flavoring and sweetening agents. Toothpastes usually additionally contain humectants and binders and water. The dentifrices herein comprise from about 0.5% to about 95% abrasive in addition to the bis-biguanide antiplaque agent.

Any abrasive polishing material which does not excessively abrade dentin can be used in these dentifrice compositions. These include, for example, calcium carbonate dicalcium orthophosphate dihydrate, calcium pyrophosphate, calcium polymetaphosphate and insoluble sodium polymetaphosphate. Preferably, however, the abrasive is one which has a high degree of compatibility with the bis-biguanide. These include, for example, condensation products of urea and formaldehyde such as disclosed by Cooley et al. in U.S. Pat. No. 3,070,510, granted Dec. 25, 1962, silica xerogels such as those disclosed in U.S. Pat. No. 3,538,230 to Pader et al., issued Nov. 3, 1970, hydrofluoric acid-treated amorphous silica abrasives such as those disclosed in U.S. Pat. No. 3,862,307 to DiGiulio, issued Jan. 21, 1975, and mineral abrasives coated with cationic polymers such as those disclosed in U.S. Ser. No. 677,592, Benedict, filed Apr. 16, 1976. The abrasives generally have a particle size of from about 0.1 to about 10 microns in diameter.

The total amount of abrasive materials in the dentifrice embodiments of this invention can range from 0.5% to 95% by weight of the dentifrice. Preferably, toothpastes contain from about 6% to about 60%, and toothpowders contain from about 20% to about 95% abrasives.

Dentifrices usually contain surface-active agents (also called sudsing agents).

Suitable surface-active agents are those which are reasonably stable and form suds throughout a wide pH range, and which will not react with the bis-biguanide compound, i.e., nonsoap nonionic, cationic, zwitterionic and amphoteric organic synthetic detergents.

The nonionic synthetic detergents which can be used with the oral compositions of the present invention may be broadly defined as compounds produced by the condensation of alkylene oxide groups (hydrophilic in nature) with an organic hydrophobic compound which may be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with a hydrophobic base formed by the condensation of propylene oxide with propylene glycol. The hydrophobic portion of the molecule which, of course, exhibits water insolubility has a molecular weight of from about 1,500 to about 1,800. The addition of polyoxyethylene radicals to this hydrophobic portion tends to increase the water solubility of the molecule as a whole and the liquid character of the products is retained up to the point where polyoxyethylene content is about 50% of the total weight of the condensation product.

Other suitable nonionic synthetic detergents include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine—products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula, $$R_1R_2R_3N \rightarrow O,$$

wherein $R_1$ contains an alkyl, alkenyl or monohydroxy alkyl radical of from about 8 to about 18 carbon atoms from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semi-polar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula $$RR'R''P \rightarrow O$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are:

dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)-phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:

octadecyl methyl sulfoxide, 2-ketotridecyl methyl sulfoxide,
3,6,9-trioxaoctadecyl 2-hydroxyethyl sulfoxide,
dodecyl methyl sulfoxide,
oleyl 3-hydroxy propyl sulfoxide,
tetradecyl methyl sulfoxide,
3-methoxytridecyl methyl sulfoxide
3-hydroxytridecyl methyl sulfoxide,
3-hydroxy-4-dodecoxybutyl methyl sulfoxide.

The zwitterionic synthetic detergents useful in the oral compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water solubilizing group, e.g., carboxy, sulfonate, sulfate, phosphate, or phosphonate. A general formula for these compounds is:

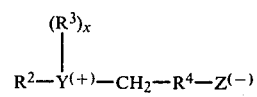

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; x is 1 when Y is a sulfur atom and 2 when Y is a nitrogen or phosphorus atom, $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradecoxylphosphonio]-2-hydroxypropane-1-phosphate;
3-[N,N-dipropyl-N-3-dodecoxy-2-hydroxypropylammonio]-propane-1-phosphonate;
3-[N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]2-hydroxypentane-1-sulfate.

The cationic synthetic detergents useful in the oral compositions of the present invention can be broadly defined as quaternary ammonium compounds having one long alkyl chain containing from about 8 to about 18 carbon atoms such as lauryl trimethylammonium chloride; cetyl pyridinium chloride; cetyl trimethylammonium bromide; di-isobutylphenoxyethyldimethylbenzylammonium chloride; coconutalkyltrimethylammonium nitrite; cetyl pyridinium fluoride; etc. Especially preferred are the quaternary ammonium fluorides described in Briner et al, U.S. Pat. No. 3,535,421, issued Oct. 20, 1970 incorporated by reference herein, where said quaternary ammonium fluorides have detergent properties.

The amphoteric synthetic detergents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxylate, sulfonate, sulfate, phosphate, or phosphonate. Examples of compounds falling within this definition are sodium 3-dodecylaminopropionate, sodium 3-dodecylamopropane sulfonate, dodecyl-beta-alanine, N-alkyl-taurines such as the one prepared by reacting dodecylamine with sodium isethionate according to the teaching of Kosmin, U.S. Pat. No. 2,658,072, issued Nov. 3, 1953, N-higher alkyl aspartic acids such as those produced according to the teaching of Lynch, U.S. Pat. No. 2,438,091, issued Nov. 16, 1948, and the products sold under the trade name "Miranol" and described in Mannheimer, U.S. Pat. No. 2,528,378 issued Oct. 31, 1950.

Many additional nonionic, cationic, zwitterionic and amphoteric synthetic detergents are known to the art and can be used as sudsing agents in the compositions herein. Further examples can be found in *McCutcheon's Detergents and Emulsifiers,* 1972 Annual, published by Allure Publishing Corporation, which is incorporated herein by reference.

The sudsing agent can be employed at levels ranging from about 0.5% to about 5.0% of the dentifrice composition.

Dentifrices normally also contain flavoring agents. Suitable flavoring agents for use in the dentifrices herein include, for example, wintergreen oil (methyl salicylate), oil of peppermint, oil of sassafras (synthetic), and oil of anise. Flavoring agents are present at a level of from 0.01% to 2.0%.

Dentifrices normally also contain sweetening agents. Suitable sweetening agents for use in dentifrices include, for example, saccharin, dextrose and levulose. The sweetening agents are used at levels of from about 0.05% to about 2%.

In toothpastes it is desirable to employ thickening agents such as hydroxyethylcellulose and water-soluble salts of cellulose ethers, including sodium carboxymethyl cellulose and sodium carboxymethylhydroxyethyl cellulose; or natural gums, including gum karaya, gum arabic and gum tragacanth. Also, colloidal magnesium aluminum silicate or finely divided silica can be used as part of the thickening agent to improve the texture of the product. Thickening agents are used at levels of from 0.1% to 5.0% of the toothpaste composition.

It is also desirable to include a humectant material in toothpastes. Suitable materials for this purpose include glycerine, sorbitol, and other edible polyhydric alcohols or mixtures thereof. These materials can comprise from about 1% to about 50% of the toothpaste composition. In addition to the aforementioned typical components of a toothpaste, water usually comprises the balance of the toothpaste, and is usually present at levels up to about 50%.

Mouthwashes generally comprise a water/ethyl alcohol solution and optionally other ingredients such as flavor, sweeteners, and humectants such as those mentioned above for dentifrices. The alcohol provides an antibacterial effect. Optionally, mouthwashes also contain sudsing agents such as those mentioned above for dentifrices Humectants such as glycerine and sorbitol give a moist feel in the mouth and are desirably also present. Antibacterial agents are sometimes incorporated into mouthwashes (or dentifrices) at levels from about 0.01% to about 2.0%.

Generally, mouthwashes suitable for use as carriers herein contain 5% to 40% ethyl alcohol, 0% to 20% (preferably 5% to 20%) glycerine or other humectant, 0% to 2% (preferably 0.1% to 2%) sudsing agent, 0% to 0.5% (preferably 0.05% to 0.5% sweetening agent such as saccharin and 0% to 0.3% (preferably 0.05% to 0.3%) flavoring agent, and the balance, water.

Chewing gum suitable for use as a carrier herein comprises a gum base and flavoring materials such as those mentioned above for dentifrices. The flavoring materials are present at a level of 0.01% to about 2.0% of the final chewing gum composition. The gum base is a chewable plastic gum material such as natural rubber, chicle, polyvinyl acetate, ester gum, coumarone resin, and paraffin wax. The gum base is typically made from a mixture of two or more plastic gum materials to achieve a preferred degree of plasticity for chewing. Optionally, corn syrup is added as a softener and binder for the chewing gum and sugar is optionally added as a filler and sweetener. A typical chewing gum suitable as a carrier herein comprises 15% to 30% gum base, 15% to 20% corn syrup, 50% to 65% sugar, and 0.05% to 1.5% flavoring materials.

Lozenges suitable as carriers herein comprise a hard sugar candy base and one or more flavoring materials. The flavoring materials are present at levels between 0.01% and 2.0%. Optionally, lozenges can contain various other materials. A typical lozenge suitable as a carrier in this invention is a hard candy comprised of a hard candy base containing 0.05% to 1.5% flavor. The hard candy base is a solidified solution of amorphous sugar which is generally formed from a sugar solution which has been cooked at high temperature so as to remove nearly all of the moisture. The flavoring materials and antiplaque agent are added before the moisture is removed. The flavoring materials mentioned hereinbefore for dentifrices are also exemplary of those suitable for use in lozenges.

When formulating the antiplaque agents of the present invention into an oral composition, the amount which is incorporated into the composition should be sufficient to provide at least 0.001 grams of antiplaque agent per usage of the composition. Thus, in dentifrices, where the amount of product used per usage is from about 1 to 4 grams, the amount of antiplaque agent in the dentifrice should be at least about 0.03%, preferably from about 0.1% to about 2%, and most preferably from about 0.5% to about 1.5%. In mouthwashes, typical usage is from about 10 to about 20 grams, and the amount of antiplaque agent in the mouthwash should be at least 0.01, preferably from about 0.5% to about 1.5%, and most preferably from about 0.1% to about 1.0%.

Typical usage of chewing gum and lozenges is from about 1 to about 4 grams and the amount of antiplaque agent in the chewing gum or lozenge should be at least about 0.03%, preferably from about 0.1% to about 2%, and most preferably from about 0.5% to about 1.5%.

Generally, oral compositions should contain from about 0.01% to about 2.5% of the antiplaque agent.

The oral compositions of the present invention can also optionally contain additional therapeutic materials for use in the oral cavity such as anticaries agents, (e.g., water-soluble fluoride such as sodium fluoride and stannous fluoride) and anticalculus agents such as trisodium ethane 1-hydroxy-1,1 diphosphonate.

This invention will be further illustrated by the following examples:

EXAMPLE I

A toothpaste is prepared according to the following formula:

| Component | Parts by weight |
|---|---|
| Sorbitol (70% soln.) | 20.00 |
| Sodium saccharin | 0.21 |
| Veegum (colloidal magnesium aluminum silicate) | 0.40 |
| Precipitated urea/formaldehyde condensate (abrasive) | 30.00 |
| Flavor | 1.00 |
| Sodium carboxymethylcellulose | 1.30 |
| Glycerine | 10.00 |
| 1,2-bis($N^5$-p-chlorophenyl-$N^1$-biguanido) ethane digluconate | 0.70 |
| Polyoxyethylene sorbitan (20) monoisostearate | 1.50 |
| Distilled water | balance to 100 |

This toothpaste, when used in the normal manner, is effective in retarding the formation of dental plaque and produces an appreciably lower level of stain on the teeth than does chlorhexidine.

EXAMPLE II

A mouthwash in accordance with the present invention is formulated as follows:

| Component | Parts by weight |
|---|---|
| Ethyl alcohol (95% in water) | 12.00 |
| Cetyl pyridinium chloride | 0.10 |
| Polyoxyethylene (20) sorbitan monooleate | 0.12 |
| Sodium hydroxide (10% in water) | 0.02 |
| Sodium saccharin | 0.055 |
| Flavoring | 0.16 |
| 1,2-bis($N^5$-p-chlorophenyl-$N^1$-biguanido) ethane dihydrochloride | 0.20 |
| Color | 0.50 |
| Sorbitol (70% in water) | 12.00 |
| Distilled water | balance to 100 |

When used in the normal manner to rinse the mouth, this product is effective in retarding the formation of dental plaque and produces an appreciably lower level of stain on the teeth than does chlorhexidine.

EXAMPLE III

A chewing gum in accordance with the present invention is formulated as follows:

| Component | Parts by weight |
|---|---|
| Gum base | 21.30 |
| Ester Gum | 6.40 |
| Coumarone resin | 9.60 |
| Dry latex rubber | 3.20 |
| Paraffin wax (M.P.180° F.) | 2.10 |
| Sugar | 58.45 |
| Corn syrup (Baume 45) | 18.20 |
| Flavoring | 1.05 |
| 1,2-bis($N^5$-p-chlorophenyl-$N^1$-biguanido) ethane diacetate | 1.00 |

Chewing this gum in the normal manner retards the formulation of dental plaque and produces appreciably less staining of the teeth than does chlorhexidine.

EXAMPLE IV

When in the preceding examples 1,2-bis($N^5$-p-chlorophenyl-$N^1$-biguanido)ethane diacetate is replaced by the digluconate or diacetate salts of the following compounds, similar results are obtained in that antiplaque performance is obtained with appreciably less staining to the teeth than is obtained if chlorhexidine is used:

1,2-bis($N^5$-m-chlorophenyl-$N^1$-biguanido)ethane
1,2-bis($N^5$-o-chlorophenyl-$N^1$-biguanido)ethane
1,2-bis($N^5$-p-hydroxyphenyl-$N^1$-biguanido)ethane
1,2-bis($N^5$-p-chlorobenzyl-$N^1$-biguanido)ethane
1,2-bis($N^5$-p-bromobenzyl-$N^1$-biguanido)ethane
1,2-bis($N^5$-p-fluorobenzyl-$N^1$-biguanido)ethane
1,2-bis($N^5$-p-chlorophenyl-$N^5$-2-ethylphenyl-$N^1$-biguanido)ethane
1,2-bis($N^5$-p-bromophenyl-$N^5$-hexyl-$N^1$-biguanido)ethane
1,2-bis($N^5$-p-chlorophenyl-$N^1$-ethyl-$N^1$-biguanido)ethane
1,2-bis($N^5$-p-methoxyphenyl-$N^1$-biguanido)ethane
1,2-bis($N^5$-p-methylphenyl-$N^1$-biguanido)ethane
1,2-bis($N^5$-3,5-dimethylphenyl-$N^1$-biguanido)ethane
1,2-bis($N^5$-2,6-dichlorophenyl-$N^1$-biguanido)ethane
1,2-bis($N^5$-2,6-dimethylphenyl-$N^1$-biguanido)ethane
1,4-bis($N^5$-p-chlorophenyl-$N^1$-biguanido)butane
1,3-bis($N^5$-p-chlorophenyl-$N^1$-biguanido)propane
1,2-bis($N^5$-p-fluorophenyl-$N^1$-biguanido)ethane
1,2-bis($N^5$-m-fluorophenyl-$N^1$-biguanido)ethane
1,3-bis($N^5$-p-fluorophenyl-$N^1$-biguanido)propane
1,4-bis($N^5$-p-fluorophenyl-$N^1$-biguanido)butane

TOOTH STAIN EVALUATION

The propensity of the compounds and compositions of the present invention to provide reduced tooth staining when employed in the oral cavity can be evaluated by means of an in vitro stain test. In such a test artificial teeth are each pretreated by rotating them overnight at 37° C. in 3 ml of the supernatant of human saliva which is previously centrifuged to remove sediment. Each such prepared tooth is then exposed to treatments involving successive soaking in two types of solutions. Each tooth is exposed first for 5 minutes in 5 ml. of a test liquid which is either a placebo solution or a solution containing a bis-biguanide being tested; followed by a 10 minute exposure in 5 ml of a coffee/tea staining solution. Soaking in each solution is followed by a swish rinse in water.

The bis-biguanide solutions tested each contain a specified concentration (generally 2.22 mM.) of the test bis-biguanide dissolved in water. The placebo solution is identical but contains no bis-biguanide. The coffee/tea staining solution is prepared by dissolving 20 grams Folgers ® Instant Coffee and 2 grams Lipton's ® Instant Tea in 1000 ml distilled water and centrifuging off the sediment. This resulting supernatant (pH, 5.1) is used as the coffee/tea stain solution.

Each tooth tested is run through two of the soaking/rinsing cycles and then graded by two experienced graders on a 0 (no stain) to 3 (very severe stain) scale. Two teeth are used for each test material and the results averaged. Some test-to-test variation in stain grade values does occur when saliva samples from different individuals are used to pretreat the test teeth. Such variation affects the absolute values of the stain grades uniformly and does not alter the stain grades of the bis-biguanide and placebo test solutions relative to each other within a given test.

Using the above procedures the following data are generated to demonstrate the reduced staining potential of 1,2-bis($N^5$-p-fluorophenyl-$N^1$-biguanido)ethane, the preferred bis-biguanide of the present invention.

TABLE I
IN VITRO STAINING OF BIS-BIGUANIDES (TEST #1)

| Test Liquid | Average Stain Grade |
|---|---|
| Water Placebo | 0.5 |
| Chlorhexidine (2.22 mM/0.2% by wt.) | 5.5 |
| 1,2-bis($N^5$-p-fluorophenyl-$N^1$-biguanido)ethane (2.22 mM/0.11% wt.) | 0.8 |

TABLE II
IN VITRO STAINING OF BIS-BIGUANIDES (TEST #2)

| Test Liquid | Average Stain Grade |
|---|---|
| Water Placebo | 1.5 |
| Chlorhexidine (0.2% by wt.) | 4.0 |
| 1,2-bis($N^5$-p-fluorophenyl-$N^1$-biguanido)ethane (1.0% by wt.) | 1.0 |

These data demonstrate that a preferred bis-biguanide of the present invention, i.e. 1,2-bis($N^5$-p-fluorophenyl-$N^1$-biguanido)ethane, produces less tooth staining than chlorhexidine, a conventional prior art bis-biguanide, both at equimolar concentrations (Test #1) and even when the p-fluorophenyl material is used at five times the chlorhexidine concentration (Test #2).

The preferred 1,2-bis($N^5$-p-fluorophenyl-$N^1$-biguanido)ethane material produces less tooth staining in in vitro testing than does its p-chloro analog, i.e. 1,2-bis($N^5$-p-chlorophenyl-$N^1$-biguanido)ethane. Furthermore, as the Table II data demonstrate, the preferred p-fluorophenyl material, in fact, is not significantly different from water in its propensity to stain teeth during the in vitro testing described.

What is claimed is:

1. Bis-biguanide compounds of the formula

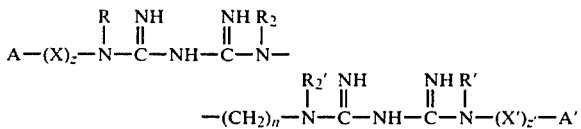

wherein A and A' each represent a p-fluorophenyl radical; wherein X and X' each represent an alkylene radical containing from 1 to 3 carbon atoms; wherein z and z' are each 0; wherein R and R' are each hydrogen; wherein $R_2$ and $R'_2$ are each hydrogen; and wherein n is an integer from 2 to 4, and the pharmaceutically acceptable salts of said bis-biguanides.

2. The compounds of claim 1 which are the water-soluble salts.

3. 1,2-bis-($N^5$-p-fluorophenyl-$N^1$-biguanido)ethane.

4. An antiplaque oral composition comprising a carrier for use in the oral cavity and from about 0.01% to about 2.5% of a bis-biguanide compound according to claim 1.

5. An antiplaque oral composition comprising a carrier for use in the oral cavity and from about 0.01% to about 2.5% of an antiplaque agent having the formula:

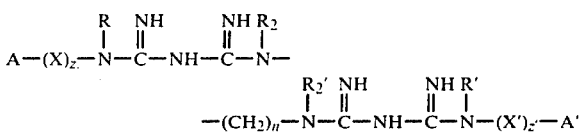

wherein A and A' each represent a p-fluorophenyl radical; wherein X and X' each represent an alkylene radical containing from 1 to 3 carbon atoms; wherein z and z' are each 0; wherein R and R' are each hydrogen; wherein $R_2$ and $R'_2$ are each hydrogen; and wherein n is an integer from 2 to 4; and the pharmaceutically acceptable salts of said antiplaque agents; said composition being substantially free of metal ion chelating agents and materials which form insoluble salts of said antiplaque agents.

6. The composition of claim 5 wherein the antiplaque agent is a water-soluble salt.

7. The composition of claim 6 wherein the salt forming anion is selected from the group consisting of acetate, gluconate and hydrochloride.

8. A dentifrice composition comprising from about 0.5% to about 95% of a dentifrice abrasive and from about 0.1% to about 2% of an antiplaque agent having the formula:

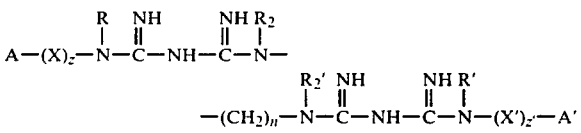

wherein A and A' each represent a p-fluorophenyl radical; wherein X and X' each represent an alkylene radical containing from 1 to 3 carbon atoms; wherein n is an integer from 2 to 4; wherein z and z' each are 0; wherein R and R' are each hydrogen; and wherein $R_2$ and $R'_2$ are each hydrogen; and the pharmaceutically acceptable salts of said antiplaque agents; said composition being substantially free of metal ion chelating agents and materials which form insoluble salts with said antiplaque agents.

9. The composition of claim 8 wherein the antiplaque agent is a water-soluble salt of 1,2-bis($N^5$-p-fluorophenyl-$N^1$-biguanido)ethane.

10. A mouthwash composition comprising:
(A) from about 5% to about 40% ethyl alcohol;
(B) from about 5% to about 20% humectant;
(C) from 0% to about 2% sudsing agent;
(D) from about 0% to about 0.5% sweetening agent;
(E) from 0% to about 0.3% flavoring agent;
(F) from about 0.05% to about 1.5% of an antiplaque agent having the formula:

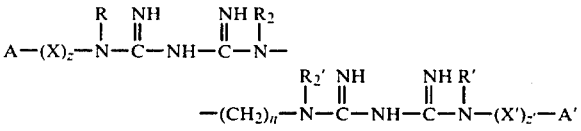

wherein A and A' each represent a p-fluorophenyl radical; wherein X and X' each represent an alkylene radical containing from 1 to 3 carbon atoms; wherein n is an integer from 2 to 4; wherein z and z' each are 0; wherein R and R' are each hydrogen; and wherein $R_2$ and $R'_2$ are each hydrogen; and the pharmaceutically acceptable salts of said antiplaque agents; and (G) the balance water;

said composition being substantially free of metal ion chelating agents and materials which form insoluble salts with the antiplaque agent.

11. The composition of claim 10 wherein the antiplaque agent is a water-soluble salt of 1,2-bis($N^5$-p-fluorophenyl-$N^1$-biguanido)ethane.

12. A chewing gum composition comprising:
(A) a gum base;
(B) from about 0.01% to about 2.0% of flavoring material; and
(C) from about 0.1% to about 2% of an antiplaque agent having the formula:

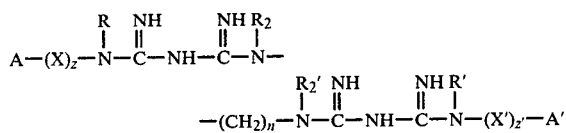

wherein A and A' each represent a p-fluorophenyl radical; wherein X and X' each represent an alkylene radical containing from 1 to 3 carbon atoms; wherein n is an integer from 2 to 4; wherein z and z' each are 0; wherein R and R' are hydrogen; and wherein $R_2$ and $R'_2$ are each hydrogen; and the pharmaceutically acceptable salts of said antiplaque agents;

said composition being substantially free of metal ion chelating agents and materials which form insoluble salts with the antiplaque agent.

13. The composition of claim 12 wherein the antiplaque agent is a water-soluble salt of 1,2-bis($N^5$-p-fluorophenyl-$N^1$-biguanido)ethane.

14. A lozenge composition comprising:
(A) a hard candy base;
(B) from about 0.01% to about 2% of a flavoring material; and
(C) from about 0.1% to about 2% of an antiplaque agent having the formula:

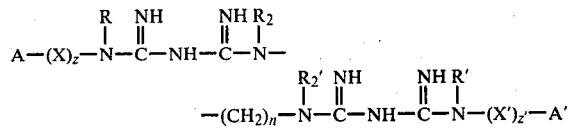

wherein A and A' each represent a p-fluorophenyl radical; wherein X and X' each represent an alkylene radical containing from 1 to 3 carbon atoms; wherein n is an integer from 2 to 4; wherein z and z' each are 0; wherein R and R' are each hydrogen; and wherein $R_2$ and $R'_2$ are each hydrogen; and the pharmaceutically acceptable salts of said antiplaque agents;

said composition being substantially free of metal ion chelating agents and materials which form insoluble salts with the antiplaque agent.

15. The composition of claim 14 wherein the antiplaque agent is a water-soluble salt of 1,2-bis($N^5$-p-fluorophenyl-$N^1$-biguanido)ethane.

* * * * *